US012041969B2

(12) United States Patent
Courbat et al.

(10) Patent No.: US 12,041,969 B2
(45) Date of Patent: *Jul. 23, 2024

(54) HEATER FOR AEROSOL-GENERATING DEVICE WITH CONNECTORS

(71) Applicant: Altria Client Services LLC, Richmond, VA (US)

(72) Inventors: Jerome Christian Courbat, Colombier (CH); Oleg Mironov, Neuchatel (CH)

(73) Assignee: Altria Client Services LLC, Richmond, VA (US)

( * ) Notice: Subject to any disclaimer, the term of this patent is extended or adjusted under 35 U.S.C. 154(b) by 450 days.

This patent is subject to a terminal disclaimer.

(21) Appl. No.: 17/465,072

(22) Filed: Sep. 2, 2021

(65) Prior Publication Data

US 2021/0400771 A1    Dec. 23, 2021

Related U.S. Application Data

(63) Continuation of application No. 16/149,647, filed on Oct. 2, 2018, now Pat. No. 11,184,954, which is a
(Continued)

(30) Foreign Application Priority Data

Oct. 3, 2017    (EP) .................................. 171946429

(51) Int. Cl.
*A24F 40/465*    (2020.01)
*A24F 40/10*    (2020.01)
(Continued)

(52) U.S. Cl.
CPC ............ *A24F 40/465* (2020.01); *A24F 40/46* (2020.01); *A24F 40/50* (2020.01); *A61M 11/042* (2014.02);
(Continued)

(58) Field of Classification Search
None
See application file for complete search history.

(56) References Cited

U.S. PATENT DOCUMENTS

| 3,621,201 A | 11/1971 | Crane et al. |
| RE44,712 E | 1/2014 | Ranish et al. |

(Continued)

FOREIGN PATENT DOCUMENTS

| CN | 106455713 A | 2/2017 |
| CN | 106686995 A | 5/2017 |

(Continued)

OTHER PUBLICATIONS

Japanese Notice of Allowance for corresponding Application No. 2020-515904, dated May 25, 2023, English translation included.
(Continued)

*Primary Examiner* — John J Norton
(74) *Attorney, Agent, or Firm* — Harness, Dickey & Pierce, P.L.C.

(57) ABSTRACT

The aerosol-generating device includes a housing, and a power supply configured to supply electrical power to a heating element by way of a transformer assembly within the housing. The transformer assembly includes a magnetic flux guide, a primary circuit including a primary winding extending around a first portion of the magnetic flux guide and electrically connected to the power supply, and a secondary circuit including a secondary winding inductively coupled to the primary winding and extending around a second portion of the magnetic flux guide. The number of turns in the primary winding is greater than the number of turns in the secondary winding. The secondary circuit includes at least two electrical contacts configured to form an electrical connection with the heating element.

22 Claims, 3 Drawing Sheets

Related U.S. Application Data continuation of application No. PCT/EP2018/075653, filed on Sep. 21, 2018.

(51) Int. Cl.
  *A24F 40/46* (2020.01)
  *A24F 40/50* (2020.01)
  *A61M 11/04* (2006.01)
  *A61M 15/06* (2006.01)
  *H01F 30/10* (2006.01)
  *H01F 38/14* (2006.01)
  *H05B 1/02* (2006.01)
  *H05B 3/03* (2006.01)
  *H05B 3/06* (2006.01)
  *H05B 3/24* (2006.01)

(52) U.S. Cl.
  CPC ............ *A61M 15/06* (2013.01); *H01F 38/14* (2013.01); *H05B 1/0227* (2013.01); *H05B 3/03* (2013.01); *H05B 3/06* (2013.01); *H05B 3/24* (2013.01); *A24F 40/10* (2020.01); *H01F 30/10* (2013.01)

(56) References Cited

U.S. PATENT DOCUMENTS

| 11,184,954 | B2* | 11/2021 | Courbat | A24F 40/46 |
|---|---|---|---|---|
| 2015/0335070 | A1 | 11/2015 | Sears et al. | |
| 2016/0021934 | A1 | 1/2016 | Cadieux et al. | |
| 2016/0270447 | A1 | 9/2016 | Borkovec | |
| 2016/0338410 | A1 | 11/2016 | Batista et al. | |
| 2017/0079326 | A1 | 3/2017 | Mironov | |
| 2017/0079330 | A1 | 3/2017 | Mironov et al. | |
| 2017/0086501 | A1 | 3/2017 | Buehler et al. | |
| 2017/0105452 | A1 | 4/2017 | Mironov et al. | |
| 2017/0202266 | A1 | 7/2017 | Sur | |
| 2018/0020737 | A1 | 1/2018 | Mironov et al. | |
| 2018/0360125 | A1 | 12/2018 | James et al. | |

FOREIGN PATENT DOCUMENTS

| CN | 107072318 A | 8/2017 |
|---|---|---|
| EP | 2456493 A1 | 5/2012 |
| JP | S53-010773 U | 1/1978 |
| JP | H51-10773 A | 4/1993 |
| JP | 2000-079483 A | 3/2000 |
| JP | 2000-079484 A | 3/2000 |
| JP | 2009-180549 A | 8/2009 |
| JP | 2017-506890 A | 3/2017 |
| JP | 2017-525348 A | 9/2017 |
| JP | 2017-537634 A | 12/2017 |
| RU | 2389419 C2 | 5/2010 |
| WO | WO-2015/117700 A1 | 8/2015 |
| WO | WO-2015177044 A1 | 11/2015 |
| WO | WO-2016014652 A1 | 1/2016 |
| WO | WO-2016/096745 A1 | 6/2016 |

OTHER PUBLICATIONS

Notice of Allowance for Chinese Application No. 201880058557.7 dated Aug. 30, 2023.
Russian Notice of Allowance for corresponding Application No. 2020115089/03(025005), dated Mar. 28, 2022, with English Translation.
Russian Office Action for corresponding Application No. 2020115089/03(025005), dated Dec. 1, 2021, with English Translation.
Japanese Office Action for corresponding Application No. 2020-515904, dated Oct. 17, 2022, English translation included.
Brazilian Office Action for corresponding Application No. 112020004146-7, dated Jul. 21, 2022, with English Translation.
Chinese Office Action for corresponding Application No. 201880058557.7, dated Feb. 25, 2023, with English Translation included herewith.
European Search Report for European Patent Application No. 17194642.9 dated Mar. 6, 2018.
International Search Report and Written Opinion for PCT Application No. PCT/EP2018/075653 dated Nov. 22, 2018.
International Preliminary Report on Patentability dated Apr. 16, 2020, issued in corresponding International Application No. PCT/EP2018/075653.
Notice of Allowance issued Feb. 26, 2024 in Korean Application No. 10-2020-7010016.

* cited by examiner

HEATER FOR AEROSOL-GENERATING DEVICE WITH CONNECTORS

CROSS-REFERENCE TO RELATED APPLICATIONS

This application is a continuation of U.S. application Ser. No. 16/149,647, filed on Oct. 2, 2018, which is a continuation of, and claims priority to, international application number PCT/EP2018/075653 filed on Sep. 21, 2018, and further claims priority under 35 USC § 119 to European patent application number 17194642.9, filed on Oct. 3, 2017, the entire contents of each of which are incorporated herein by reference.

FIELD

Example embodiments relate to aerosol-generating devices and systems, such as handheld electrically operated aerosol-generating devices and systems. Example embodiments relate to aerosol-generating devices and cartridges configured to connect to said devices, where the cartridges contain a supply of aerosol-forming substrate and a heater.

DESCRIPTION OF RELATED ART

Handheld electrically operated aerosol-generating systems that consist of a device portion comprising a battery and control electronics, a cartridge portion comprising a supply of aerosol-forming substrate held in a storage portion and an electrically operated heater assembly acting as a vaporizer are known. A cartridge comprising both a supply of aerosol-forming substrate held in the storage portion and a vaporizer is sometimes referred to as a "cartomizer".

The heater assembly may include a fluid-permeable heating element that is in contact with the aerosol-forming substrate held in the storage portion. The fluid-permeable heating element can be an array of electrically conductive filaments that form a mesh. Electrical power is supplied to the mesh to vaporize fluid held in the storage portion.

Electrically operated aerosol-generating systems heating elements, such as a mesh, are designed to have a relatively high electrical resistance. This is so that a large proportion of the electrical losses in the system occur at the heating element. Having a large proportion of the electrical losses in the system occur at the heating element can improve the circuit efficiency, and reduce the heating of unwanted areas.

SUMMARY

At least one example embodiment relates to an aerosol-generating device.

In one embodiment, the aerosol-generating device includes a housing; and a power supply configured to supply electrical power to a heating element by way of a transformer assembly within the housing, wherein the transformer assembly includes a magnetic flux guide; a primary circuit including a primary winding extending around a first portion of the magnetic flux guide and electrically connected to the power supply; and a secondary circuit including a secondary winding inductively coupled to the primary winding and extending around a second portion of the magnetic flux guide; wherein the number of turns in the primary winding is greater than the number of turns in the secondary winding; and wherein the secondary circuit includes at least two electrical contacts configured to form an electrical connection with the heating element.

In one embodiment, the heating element is integral to the at least two electrical contacts of the secondary circuit.

In one embodiment, the aerosol-generating device includes a storage portion configured to contain an aerosol-forming substrate, and wherein the heating element is arranged to heat the aerosol-forming substrate.

In one embodiment, the housing has a first portion configured to connect to a removable cartridge including the heating element, and wherein the at least two electrical contacts are configured to form an electrical connection with the heating element when the removable cartridge is connected to the aerosol-generating device.

In one embodiment, the removable cartridge includes a storage portion configured to contain an aerosol-forming substrate, and wherein the heating element is arranged to heat the aerosol-forming substrate.

In one embodiment, at least a portion of each electrical contact extends from the first portion of the housing of the aerosol-generating device.

In one embodiment, the at least two electrical contacts are configured to directly contact the heating element when the removable cartridge is connected to the aerosol-generating device.

In one embodiment, when the removable cartridge is connected to the aerosol-generating device, the heating element forms an electrically conductive bridge between the at least two electrical contacts to complete the secondary circuit.

In one embodiment, each of the at least two electrical contacts is an electrical contact blade.

In one embodiment, each of the at least two electrical contacts has a pointed leading edge configured to form an electrical connection with the heating element.

In one embodiment, each of the at least two electrical contacts includes tungsten.

In one embodiment, the magnetic flux guide includes a looped magnetic core.

In one embodiment, a first portion and a second portion of the magnetic flux guide are located on respectively opposing sides of the looped magnetic core.

In one embodiment, the secondary winding includes of a single turn.

In one embodiment, the heating element is a substantially flat electrically conductive and fluid permeable heating element.

BRIEF DESCRIPTION OF THE DRAWINGS

Features described in relation to one example embodiment may equally be applied to other example embodiments.

Example embodiments will now be described with reference to the following drawings.

DETAILED DESCRIPTION

Figure 1:
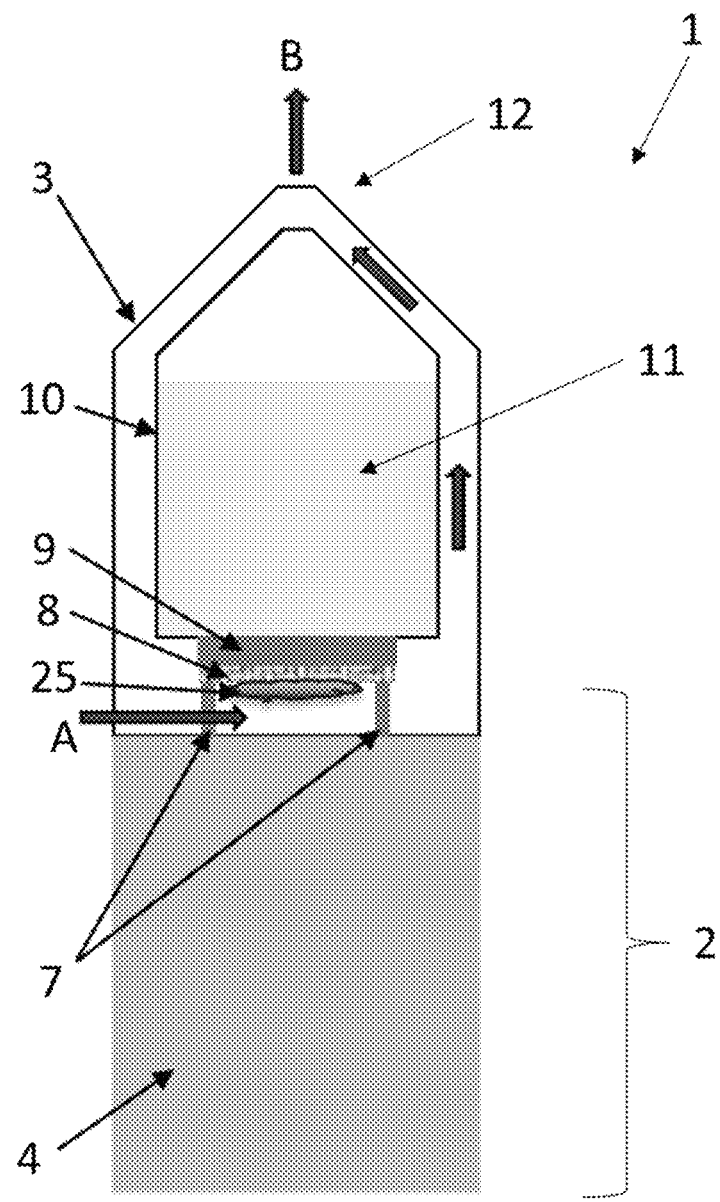
FIG. 1 illustrates an aerosol-generating device according to a first embodiment of the present invention, and a removable cartridge, in accordance with an example embodiment.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, regions, layers and/or sections, these elements and/or sections should not be limited by these terms. These terms are only used to distinguish one element or section from another section. Thus, a first element, or section discussed below could be termed a second element, or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Designing certain heating elements, such as meshes, to have a relatively high electrical resistance can be problematic. For example, it may imposes restrictions on the material that heating element can be formed from. As another example, it may require the heating element to have dimensions that are difficult or costly to obtain. In the case of a heating mesh, it may require the mesh filaments to have very small diameters. This may make the mesh difficult to manufacture. This may also make the mesh structurally fragile. This may also inhibit the design flexibility for the mesh.

The example embodiments provide an improved electrically powered heater arrangement for an aerosol-generating device, that would allow for greater flexibility in the design and materials that can be chosen for the heating element.

According to a first aspect of the example embodiments, there is provided an aerosol-generating device (also referred to as a "vapor-generating system," or vaporizer), including a housing; and a power supply configured to supply electrical power to a heating element by way of a transformer assembly within the housing. The transformer assembly includes a magnetic flux guide; a primary circuit comprising a primary winding extending around a first portion of the magnetic flux guide and electrically connected to the power supply; and a secondary circuit comprising a secondary winding inductively coupled to the primary winding and extending around a second portion of the magnetic flux guide. The number of turns in the primary winding is greater than the number of turns in the secondary winding. The secondary circuit may include at least two electrical contacts configured to form an electrical connection with a heating element.

By providing electrical power to the heating element by way of a transformer assembly within the housing, a suitably high current can be supplied to the heating element, without significant losses occurring elsewhere in the power circuit. In particular, the transformer assembly may enable relatively low currents to flow in the primary circuit, thus reducing losses in the wires of said circuit. In an embodiment, the number of turns in the primary winding is greater than the number of turns in the secondary winding, and because the primary winding may be inductively coupled to the secondary winding, a higher current can flow in the secondary circuit, and may supply the heating element with sufficient power. In an example embodiment, the heating element can have a lower resistance than that of heating elements in known aerosol-generating devices or systems, without a significant loss in system efficiency. This enables greater flexibility in the design and materials that can be chosen for the heating element. This is particularly relevant when the heating element is a substantially flat electrically conductive and fluid permeable heating element, such as a mesh.

In an example embodiment the number of turns in the primary winding is greater than the number of turns in the secondary winding. In an embodiment, the number of turns in the primary winding is at least 2 times greater than the number of turns in the secondary winding. In another example embodiment, the number of turns in the primary winding is at least 4 times greater than the number of turns in the secondary winding. In another example embodiment, the number of turns in the primary winding is at least 5 times greater than the number of turns in the secondary winding. In an example embodiments, the secondary winding consists of only a single turn. In another example embodiment, the number of turns in the primary winding is no more than 20 times greater than the number of turns in the secondary winding.

In an example embodiment, the heating element is provided as an integral part of the aerosol-generating device.

Therefore, in a first set of example embodiments, the aerosol-generating device may include the heating element, and the heating element is permanently affixed to the at least two electrical contacts of the secondary circuit. In an embodiment, the heating element forms an electrically conductive bridge between the at least two electrical contacts to complete the secondary circuit. In another embodiment, the at least two electrical contacts are in direct contact with the heating element. In such embodiments, the heating element forms an electrically conductive bridge between the at least two electrical contacts to complete the secondary circuit.

In the first set of example embodiments, the device may include a storage portion configured to contain an aerosol-forming substrate (also referred to as a "pre-vapor formulation"), and the electrically operable heating element is arranged to heat the aerosol-forming substrate. The storage portion may be contained within the housing. The heating element may be contained within the housing. In the first set of example embodiments, the storage portion may be configured to be refilled with aerosol-forming substrate. That is, when at least some of the aerosol-forming substrate has been vaporized by the heating element, the storage portion may be refilled with more aerosol-forming substrate.

In an example embodiment, the heating element is provided as an integral part of the removable cartridge of an aerosol-generating device.

In a second set of example embodiments, the housing has a first portion configured to connect to a removable cartridge, wherein said removable cartridge has the electrically operable heating element. In an embodiment, the at least two electrical contacts are configured to form an electrical connection with the heating element when the cartridge is connected to the aerosol-generating device. In an embodiment, at least a portion of each electrical contact extends from the first portion of the housing of the aerosol-generating device. In another embodiment, the at least two electrical contacts are configured to directly contact the heating element when the cartridge is connected to the device. In another embodiment, when the cartridge is connected to the device, the heating element forms an electrically conductive bridge between the at least two electrical contacts to complete the secondary circuit.

The removable cartridge may include a storage portion configured to contain the aerosol-forming substrate. The electrically operable heating element of the cartridge may be arranged to heat the aerosol-forming substrate.

In the second set of example embodiments, when the aerosol-forming substrate has been vaporized by the heating element of the cartridge, the cartridge can be disconnected from the housing of the device, and a new replacement cartridge can be connected to the device.

In an example embodiment, the storage portion may include a host material made from the capillary medium for retaining liquid aerosol-forming substrate. The host material piece may be provided at least partially in contact with the heating element.

In an example embodiment, the cartridge or the aerosol-generating device may include a transport material piece made from a capillary medium for transporting liquid aerosol-forming substrate from the host material piece to the heating element. The transport material piece may be provided in contact with the heating element. In an embodiment, the transport material piece is arranged between the heating element and the host material piece. In this case, the host material may not be in direct contact with the heating element.

The transport material piece may be made of a material capable of guaranteeing that there is liquid aerosol-forming substrate in contact with at least a portion of the surface of the heating element. The transport material piece may be in contact with the electrically conductive filaments of the heating element. The transport material piece may extend into interstices between the filaments. The heating element may draw liquid aerosol-forming substrate into the interstices by capillary action.

A capillary material is a material that may actively convey liquid from one end of the material to another. The capillary material may be oriented, directly or indirectly via another capillary medium, in contact with a liquid storage portion to convey liquid aerosol-forming substrate towards the heating element.

The capillary material may include even more than two capillary materials, including one or more layers of the capillary material directly in contact with the mesh, array or fabric of electrically conductive filaments of the heating element in order to promote aerosol generation.

The capillary material may have a fibrous or spongy structure. The capillary material may include a bundle of capillaries. For example, the capillary material may include a plurality of fibers or threads or other fine bore tubes. The fibers or threads may be generally aligned to convey liquid aerosol-forming substrate towards the heating element. Alternatively, the capillary material may include sponge-like or foam-like material. The structure of the capillary material forms a plurality of small bores or tubes, through which the liquid aerosol-forming substrate can be transported by capillary action. The capillary material may include any suitable material or combination of materials. Examples of suitable materials are a sponge or foam material, ceramic- or graphite-based materials in the form of fibers or sintered powders, foamed metal or plastics material, a fibrous material, for example made of spun or extruded fibers, such as cellulose acetate, polyester, or bonded polyolefin, polyethylene, terylene or polypropylene fibers, nylon fibers or ceramic. The capillary material may have any suitable capillarity and porosity so as to be used with different liquid physical properties. The liquid aerosol-forming substrate has physical properties, including but not limited to viscosity, surface tension, density, thermal conductivity, boiling point and vapor pressure, which allow the liquid aerosol-forming substrate to be transported through the capillary medium by capillary action.

In an example embodiment, each of the at least two electrical contacts is an electrical contact blade. The electrical contact blade may be substantially planar. The substantially planar contact blade has a width, a length and a thickness. In an embodiment, the contact blade has a thickness that is less than 1 millimeter, or about 0.5 millimeters. In an embodiment, the contact blade has a leading edge configured to engage with at least part of the heating element and form an electrical connection with the heating element. In an embodiment, the leading edge is elongated. This can be particularly advantageous when the heating element is a mesh, because the elongated leading edge can help to more effectively distribute the current across the filaments of the mesh.

In an example embodiment, each contact blade has a pointed leading edge configured to form an electrical connection with the heating element. This can be particularly advantageous when the pointed leading edge is configured to directly contact the heating element, because the pointed leading edge of the contact blade can deform the portion of the heating element that it comes into contact with, and thus form a better electrical connection with the heating element. A better electrical connection can be achieved because the contact surface area is increased. This may be particularly relevant when the heating element is a mesh, such as a mesh formed from stainless steel or graphite.

In an example embodiment, each of the at least two electrical contacts may include tungsten, or each of the at least two electrical contacts consist of tungsten. Tungsten is a particularly hard wearing material. It can therefore advantageously form a good electrical connection with the heating element. This can be particularly advantageous where the heating element is provided on a removable cartridge, because it ensures that the contact is less likely to become damaged during repeated attachment and removal of the cartridge or cartridges. Tungsten also advantageously has a relatively low electrical resistance.

In an embodiment, each of the at least two electrical contacts is fixed relative to the housing. In an embodiment, at least a portion of each of the at least two electrical contacts extends beyond the outer housing.

In an example embodiment, each of the at least two electrical contacts is an electrical contact blade, the secondary winding may consist of a single turn formed by the contact blades and an electrically conductive track electrically connecting the contact blades. The track may be a single wire.

In an example embodiment, the primary winding may extend around a first portion of the magnetic flux guide and the secondary winding may extend around a second portion of the magnetic flux guide.

In an example embodiment, the magnetic flux guide may be formed as a single element or as two of more discrete elements. The magnetic flux guide may include a looped magnetic core. The looped magnetic core may have a completely toroidal shape. In another example embodiment, the looped magnetic core may include two substantially parallel bars, with each end of one bar connected to a respective end of the other bar to form a looped arrangement.

In an example embodiment, the first and second portions of the magnetic flux guide may be located on respectively opposing sides of the looped magnetic core. This can improve the inductive coupling between the primary winding and the secondary winding.

The magnetic flux guide may include a ferrite material, or consists of a ferrite material. Suitable ferrite materials include iron (III) oxide and barium carbonate.

The electrically operated heating element may have a number of different configurations. In an example embodiment, the heating element may include a coil. The coil may extend around a wick which is configured to transport liquid from a storage portion containing a liquid aerosol-generating substrate to a location adjacent to the coil. The coil heating element can be used to vaporize the transported liquid to produce an aerosol.

In an example embodiment, the heating element is a substantially flat electrically conductive and fluid permeable heating element, such as a mesh. In an embodiment, the heating element may be an array of filaments, for example arranged parallel to each other.

In an example embodiment, the electrically operable heating element includes a magnetic material. Suitable magnetic materials for the heating element include ferrites, electrical steel, and permalloy.

The aerosol generating device of the present invention may include a power supply configured to supply electrical power to the heating element by way of the transformer assembly. In an example embodiment, the power supply may be electrically connected to the primary winding. The power supply may include a power source. The power source may be a battery, such as a lithium iron phosphate battery. In another example embodiment, the power source may be another form of charge storage device such as a capacitor. The power source may require recharging and may have a capacity that allows for the storage of enough energy for one or more vaping experiences. In an example embodiment, the power supply may have sufficient capacity to allow for the continuous generation of aerosol for a period of around six minutes, or for a period that is a multiple of six minutes. In another example embodiment, the power supply may have sufficient capacity to allow for a predetermined number of discrete activations of the heater.

In an example embodiment, the power supply includes power supply circuitry, which electrically connects the power source to the primary winding. In an embodiment, the power supply circuitry may include control electronics. In an embodiment, the control electronics are configured to regulate a supply of power to the primary winding, and consequently a supply of power to the heater element by way of the transformer assembly. Power may be supplied to the primary winding continuously following activation of the device or may be supplied intermittently, such as on an activation by activation basis.

In an example embodiment the heating element may be cut so as to provide open areas when mounting the heating element across the first cap opening. In an embodiment, the open areas may be manufactured by cutting beveled window slots out of each side of the heating element. In an embodiment, the filaments may form a mesh. The mesh may be woven or non-woven. The mesh may be formed using different types of weave or lattice structures. In another example embodiment, the electrically conductive heating element consists of an array of filaments arranged parallel to one another. The mesh, array or fabric of electrically conductive filaments may also be characterized by its ability to retain liquid.

In an example embodiment, a substantially flat heating element may be constructed from a wire that is formed into a wire mesh. In an embodiment, the mesh has a plain weave design. In an embodiment, the heating element is a wire grill made from a mesh strip.

The electrically conductive filaments may define interstices between the filaments and the interstices that may have a width of between 10 micrometer and 100 micrometer. In an embodiment, the filaments give rise to capillary action in the interstices, so that in operation, liquid to be vaporized is drawn into the interstices, increasing the contact area between the heating element and the liquid aerosol-forming substrate.

The electrically conductive filaments may form a mesh of size between 60 and 240 filaments per centimeter (+/−10 percent). In an embodiment, the mesh density is between 100 and 140 filaments per centimeter (+/−10 percent) or in another embodiment the mesh density is approximately 115 filaments per centimeter. The width of the interstices may be between 100 micrometer and 25 micrometer, or between 80 micrometer and 70 micrometer, or approximately 74 micrometer. The percentage of open area of the mesh, which is the ratio of the area of the interstices to the total area of the mesh may be between 40 percent and 90 percent, or between 85 percent and 80 percent, or approximately 82 percent. Throughout this specification, the density of such a mesh is referred to as "first mesh density".

Additionally, in example embodiments the mesh may have one or more sections with increased mesh density, referred to as "second mesh density", where the interstices between the filaments are below 5 micrometer, or below 2 micrometer, or approximately 1 micrometer. The one or more sections of the mesh with increased mesh density are referred to as "dense areas" throughout this specification.

The electrically conductive filaments may have a diameter of between 8 micrometer and 100 micrometer, or between 10 micrometer and 50 micrometer, or between 12 micrometer and 25 micrometer. The filaments may have a round cross-section or may have a flattened cross-section.

The area of the mesh, array or fabric of electrically conductive filaments may be small, for example less than or equal to 50 square millimeters, or less than or equal to 25 square millimeters, or approximately 15 square millimeters. The size is chosen such to incorporate the heating element into a handheld system. Sizing of the mesh, array or fabric of electrically conductive filaments less or equal than 50 square millimeters reduces the amount of total power required to heat the mesh, array or fabric of electrically conductive filaments while still ensuring sufficient contact of the mesh, array or fabric of electrically conductive filaments to the liquid aerosol-forming substrate. The mesh, array or fabric of electrically conductive filaments may, for example, be rectangular and have a length between 2 millimeter to 10 millimeter and a width between 2 millimeter and 10 millimeter. In an embodiment, the mesh has dimensions of approximately 5 millimeter by 3 millimeter. The mesh or array of electrically conductive filaments may cover an area of between 30 percent and 90 percent of the open area of the first cap opening across which the heating element extends. In another embodiment, the mesh or array of electrically conductive filaments covers an area of between 50 percent and 70 percent of the open area of the first cap opening or the mesh or array of electrically conductive filaments covers an area of between 55 percent and 65 percent of the open area of the first cap opening.

The filaments of the heating element may be formed from any material with suitable electrical properties. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may include doped or undoped ceramics. Examples of suitable doped ceramics include doped silicon carbides. Examples of suitable metals include titanium, zirconium, tantalum and metals from the platinum group.

Examples of suitable metal alloys include stainless steel, constantan, nickel-, cobalt-, chromium-, aluminum-, titanium-, zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminum based alloys and iron-manganese-aluminum based alloys. Timetal® is a registered trade mark of Titanium Metals Corporation. The filaments may be coated with one or more insulators. Example materials for the electrically conductive filaments are stainless steel and graphite, or 300 series stainless steel like AISI 304, 316, 304L, 316L. Additionally, the electrically conductive heating element may include combinations of the above materials. A combination of materials may be used to improve the control of the resistance of the substantially flat heating element. For example, materials with a high intrinsic resistance may be combined with materials with a low intrinsic resistance. This may be advantageous if one of the materials is more beneficial from other perspectives, for example reasons may include price, machinability or other physical and chemical parameters. A substantially flat filament arrangement with increased resistance reduces parasitic losses. High resistivity heaters allow more efficient use of battery energy.

In an example embodiment, the filaments are made of wire. In another example embodiment, the wire is made of metal, or stainless steel.

In an example embodiment, the electrical resistance of the mesh, array or fabric of electrically conductive filaments of the heating element may be between 0.1 Ohms and 2 Ohms. In another embodiment, the electrical resistance is equal or greater than 0.1 Ohms. In another embodiment, the electrical resistance of the mesh, array or fabric of electrically conductive filaments is between 0.1 Ohms and 0.6 Ohms, or about 0.3 Ohms. The electrical resistance of the mesh, array or fabric of electrically conductive filaments may be at least an order of magnitude, or at least two orders of magnitude, greater than the electrical resistance of electrically conductive contact areas. This ensures that the heat generated by passing current through the heating element is localized to the mesh or array of electrically conductive filaments. It is advantageous to have a low overall resistance for the heating element if the system is powered by a battery. A low resistance, high current system allows for the delivery of high power to the heating element. This allows the heating element to heat the electrically conductive filaments to a desired temperature quickly.

As noted above, in a second set of example embodiments, an aspect of the example embodiments concerns an aerosol-generating device including a housing having a first portion configured to connect to a removable cartridge, wherein said removable cartridge has the electrically operable heating element.

Accordingly, according to a second aspect of the example embodiments there is provided an aerosol-generating device according to the first aspect of the invention, and a removable cartridge configured to connect to a first portion of the housing of the aerosol-generating device, the cartridge including a storage portion containing an aerosol-forming substrate, and an electrically operable heating element arranged to heat the aerosol-forming substrate.

Features of one aspect of the example embodiments may be applied to the other aspects of the example embodiments.

Example Structural Embodiments

FIG. 1 illustrates an aerosol-generating device according to a first embodiment of the present invention, and a removable cartridge, in accordance with an example embodiment. The devices includes an aerosol-generating system 1 including an aerosol generating device 2 and a removable cartridge 3, which is connected to the device 2. The device 2 includes a housing 4. A power supply 5 and transformer assembly 6 are contained within the housing 4. The power supply 5 and the majority of the transformer assembly 6 are not visible in FIG. 1, but can be best seen from FIG. 2.

Figure 2:
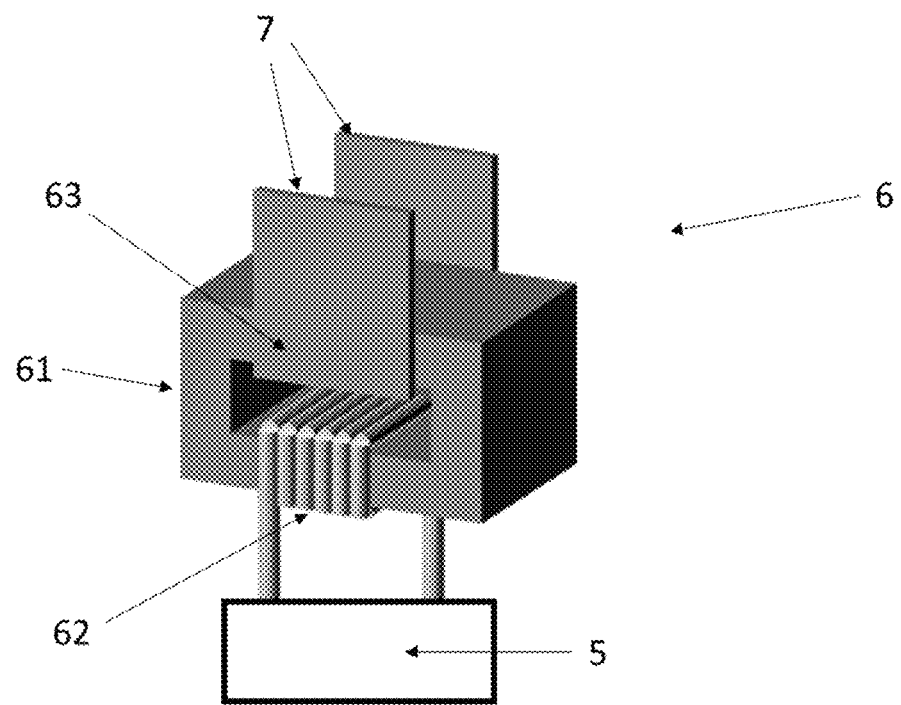
FIG. 2 illustrates a perspective view of the transformer assembly of the device of FIG. 1, in accordance with an example embodiment.

FIG. 2 illustrates a perspective view of the transformer assembly of the device of FIG. 1, in accordance with an example embodiment.

The transformer assembly 6 of FIG. 2 includes a magnetic flux guide 61 in the form of a looped magnetic core. The transformer assembly 6 also includes a primary circuit comprising a primary winding 62 extending around a first portion of the magnetic flux guide 61 and electrically connected to the power supply 5. The transformer assembly 6 also includes a secondary circuit comprising a secondary winding 63 inductively coupled to the primary winding and extending around a second portion of the magnetic flux guide 61. The number of turns in the primary winding 62 is greater than the number of turns in the secondary winding 63. In this example embodiment, the primary winding 62 has six turns, whereas the secondary winding 63 only has a single turn. The single turn of the secondary winding 63 is formed by two contact blades 7 and an electrically conductive track (not visible), which electrically connects the contact blades 7. The track extends through the hollow center of the looped magnetic core 61.

As best seen from FIG. 1, the two electrical contacts 7 are configured to form an electrical connection with a heating element 8, when the cartridge 3 is connected to the device 2.

In operation, air is drawn from a mouth end 12 of the cartridge 3. This causes air to be drawn in through inlet A and travel past the mesh 8. The mesh 8 may be electrically powered by the power supply 5 with an alternating current via the transformer assembly 6. This causes the mesh 8 to heat the liquid aerosol-forming substrate that has been transferred to the mesh 8 by the transport material 9. The liquid is then vaporized by the mesh 8 to form a vapor, which is transported by the passing air along a flow path to outlet B at the mouth end 12 of the cartridge 3.

Figures 3A, 3B:
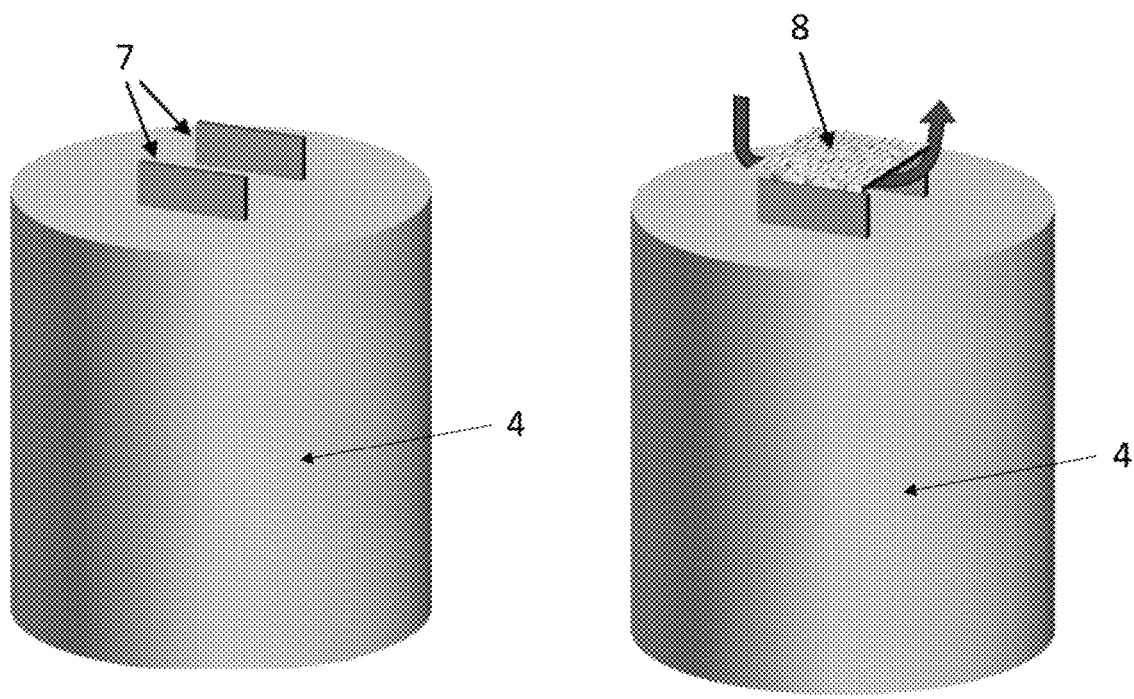
FIG. 3A illustrates a perspective view of portions of the aerosol-generating article of FIG. 1, in accordance with an example embodiment.
FIG. 3B illustrates a perspective view of portions of the aerosol-generating article of FIG. 1, in accordance with an example embodiment.

FIG. 3A illustrates a perspective view of portions of the aerosol-generating article of FIG. 1, in accordance with an example embodiment. FIG. 3B illustrates a perspective view of portions of the aerosol-generating article of FIG. 1, in accordance with an example embodiment.

As best seen from FIG. 3B, the heating element 8, in this embodiment, is provided in the form of a substantially flat electrically conductive and fluid permeable mesh. The curved arrow in FIG. 3B indicates the flow path of air when the device is in operation. The contact blades 7 are substantially planar, and each have a longitudinal leading edge 71 which engages with a respective edge of the mesh 8. The mesh 8 is adjacent to a transport material 9, which is configured to transfer liquid aerosol forming substrate 11 from a storage portion 10 of the cartridge 3 to the mesh 8.

Figure 4:
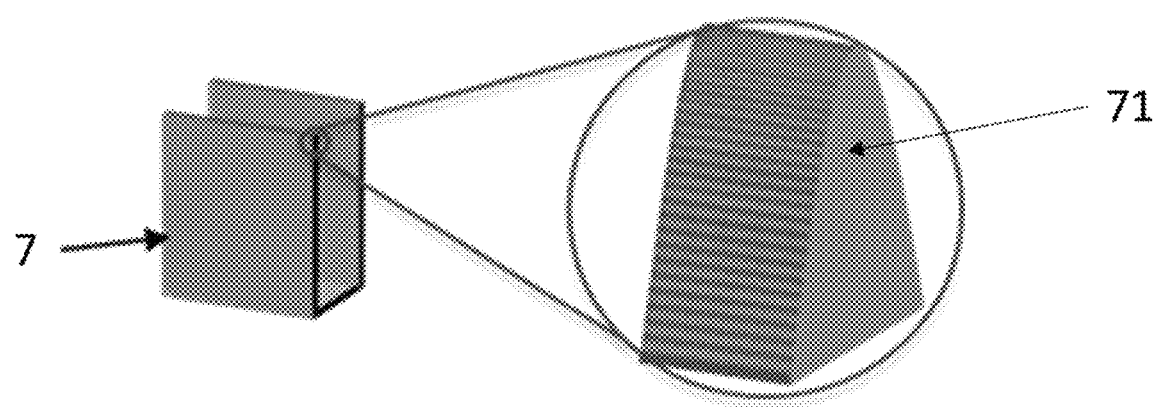
FIG. 4 illustrates an enlarged view of the leading edge of a contact blade of the device of FIG. 1, in accordance with an example embodiment.

FIG. 4 illustrates an enlarged view of the leading edge of a contact blade of the device of FIG. 1, in accordance with an example embodiment.

FIG. 4 shows an enlarged view of a portion of the leading edge of one of the contact blades 7 of FIG. 1. As can be seen from FIG. 4, the leading edge has a pointed tip 71. This can help the blade 7 to form a better electrical contact with the heating mesh 8.

The voltage and current relationship in the transformer assembly can be expressed as:

$$\frac{V_P}{V_S} = \frac{I_P}{I_S} = \frac{N_P}{N_S}$$

where:
Vp is the voltage at the primary side of the transformer assembly;

Vs is the voltage at the secondary side of the transformer assembly;
Ip is the current at the primary side; Is is the current at the secondary side;
Np is the number of turns of the primary winding; and
Ns is the number of turns of the secondary winding.

In the example embodiment of FIG. 1, Np=6 and Ns=1. This means that the relationship can be expressed as:

$$Is=6Ip \text{ and } Vs=Vp/6$$

However, the impedance of the primary winding as function of the secondary winding is defined as:

$$Zp=Zs\times(Np/Ns)2 \rightarrow Zp=Zs\times(Np)2$$

Accordingly, the impedance seen at the primary side of the transformer assembly can be increased proportionally to the square of the number of turns of the primary winding. Thus, in the example embodiment of FIG. 1, for a desired secondary impedance of approximately 0.3Ω, a primary impedance of 10.8Ω is required. This results in a smaller driving current being used to heat the mesh compared to that which would be needed if the mesh were to be driven with direct current. Lower losses can also be achieved along the electrical connections and at the contacts.

The specific embodiments and examples described above illustrate but do not limit the example embodiments. It is to be understood that other embodiments may be made, and the specific embodiments and examples described herein are not exhaustive.

We claim:

1. An aerosol-generating system comprising:
a housing;
a power supply within the housing and configured to supply electrical power to a heating element;
a transformer assembly within the housing, the transformer assembly including,
a magnetic flux guide;
a primary circuit including a primary winding extending around a first portion of the magnetic flux guide and electrically connected to the power supply; and
a secondary circuit inductively coupled to the primary winding and extending around a second portion of the magnetic flux guide, the secondary circuit including at least two electrical contact blades and an electrically conductive track electrically connecting the electrical contact blades; and
a cartridge configured to be removably coupled to a first portion of the housing.

2. The aerosol-generating system of claim 1, wherein the at least two electrical contact blades are configured to form an electrical connection with the heating element.

3. The aerosol-generating system of claim 1, wherein the heating element is integral to the at least two electrical contact blades of the secondary circuit.

4. The aerosol-generating system of claim 3, further comprising:
a storage portion configured to contain an aerosol-forming substrate, and
wherein the heating element is arranged to heat the aerosol-forming substrate.

5. The aerosol-generating system of claim 1, wherein the at least two electrical contact blades are configured to form an electrical connection with the heating element when the cartridge is connected to the housing.

6. The aerosol-generating system of claim 5, wherein the cartridge includes a storage portion configured to contain an aerosol-forming substrate, and wherein the heating element is arranged to heat the aerosol-forming substrate.

7. The aerosol-generating system of claim 5, wherein at least a portion of each of the at least two electrical contact blades extends from the first portion of the housing.

8. The aerosol-generating system of claim 5, wherein the at least two electrical contact blades are configured to directly contact the heating element when the cartridge is connected to the housing.

9. The aerosol-generating system of claim 4, wherein, when the cartridge is connected to the housing, the heating element forms an electrically conductive bridge between the at least two electrical contact blades to complete the secondary circuit.

10. The aerosol-generating system of claim 1, wherein each of the at least two electrical contact blades has a pointed leading edge configured to form an electrical connection with the heating element.

11. The aerosol-generating system of claim 1, wherein each of the at least two electrical contact blades includes tungsten.

12. The aerosol-generating system of claim 1, wherein the magnetic flux guide includes a looped magnetic core.

13. The aerosol-generating system of claim 12, wherein the first portion and the second portion of the magnetic flux guide are located on respectively opposing sides of the looped magnetic core.

14. The aerosol-generating system of claim 1, wherein the secondary winding includes a single turn.

15. The aerosol-generating system of claim 1, wherein the heating element is a flat electrically conductive and fluid permeable heating element.

16. The aerosol-generating system of claim 1, wherein a number of turns in the primary winding is at least two times greater than a number of turns in the secondary winding.

17. The aerosol-generating system of claim 1, wherein the aerosol-generating system comprises the heating element, and the heating element is permanently affixed to the at least two electrical contact blades of the secondary circuit.

18. A method of operating an aerosol-generating device comprising:

drawing air through an inlet in a housing of the aerosol-generating device;
activating a power supply configured to supply electrical power to a heating element by way of a transformer assembly within the housing, the transformer assembly including,
a magnetic flux guide;
a primary circuit including a primary winding extending around a first portion of the magnetic flux guide and electrically connected to the power supply; and
a secondary circuit including a secondary winding inductively coupled to the primary winding and extending around a second portion of the magnetic flux guide, the secondary winding comprising at least two electrical contact blades and an electrically conductive track electrically connecting the electrical contact blades;
directing the air and between the at least two electrical contact blades;
transporting an aerosol-forming substrate to the heating element; and
heating the aerosol-forming substrate to form a vapor.

19. The method of claim 18, further comprising coupling the heating element to the at least two electrical contact blades.

20. The method of claim 18, further comprising:
coupling a removable cartridge to the housing; and
forming an electrical connection between the at least two electrical contact blades and the heating element when the removable cartridge is connected to the housing.

21. The method of claim 20, wherein the transporting the aerosol-forming substrate includes transporting the aerosol-forming substrate from a storage portion in the removable cartridge to the heating element by a transport material.

22. The method of claim 18, wherein the transporting the aerosol-forming substrate includes transporting the aerosol-forming substrate from a storage portion in the housing to the heating element by a transport material.

* * * * *